United States Patent [19]

Landscheidt et al.

[11] Patent Number: 5,412,147
[45] Date of Patent: May 2, 1995

[54] PROCESS FOR THE CONTINUOUS PREPARATION OF ALKYL NITRITES

[75] Inventors: Heinz Landscheidt, Duisburg; Paul Wagner, Düsseldolf; Alexander Klausener, Stolberg, all of Germany

[73] Assignee: Bayer Aktiengesellschaft, Leverkusen, Germany

[21] Appl. No.: 157,779

[22] Filed: Nov. 24, 1993

[30] Foreign Application Priority Data

Dec. 1, 1992 [DE] Germany ............... 42 40 311.1

[51] Int. Cl.$^6$ ............................................. C07C 203/00
[52] U.S. Cl. ......................................................... 558/488
[58] Field of Search ............................................ 558/488

[56] References Cited

U.S. PATENT DOCUMENTS

| | | | |
|---|---|---|---|
| 2,739,166 | 3/1956 | Treacy | 558/488 |
| 2,831,882 | 4/1958 | Spaeth | 558/488 |
| 4,353,843 | 10/1982 | Doumaux, Jr. et al. | 558/488 |
| 4,908,466 | 3/1990 | Nelson | 558/488 |

FOREIGN PATENT DOCUMENTS 310191 9/1988 European Pat. Off.
1156775 10/1961 Germany .

OTHER PUBLICATIONS

Chemical Abstract, Nitrites, Ger. 1,156,775.

*Primary Examiner*—Robert L. Stoll
*Assistant Examiner*—Valerie Fee
*Attorney, Agent, or Firm*—William C. Gerstenzang; Sprung Horn Kramer & Woods

[57] ABSTRACT

$C_1$–$C_6$-Alkyl nitrites can be prepared by reacting nitrogen dioxide with $C_1$–$C_6$-alcohols, by, in a counterflow-operated column, feeding the alcohol or an alcohol/water mixture into the upper part of the column and the nitrogen dioxide or a nitrogen dioxide/inert gas mixture into the lower part of the column. The resulting alkyl nitrite is removed from the column as the top product and the co-formed nitric acid is removed from the column as the bottom product.

17 Claims, No Drawings

PROCESS FOR THE CONTINUOUS PREPARATION OF ALKYL NITRITES

BACKGROUND OF THE INVENTION

1. Field of the Invention

The present invention relates to a process for the preparation of alkyl nitrites from nitrogen dioxide and alcohols in a counterflow-operated column.

Alkyl nitrites (alkyl esters of nitrous acid) have a wide variety of uses, for example, as additives for engine oils, as stabilizers for unsaturated organic compounds, as spasmolytics, as reagents for oximations, nitrosations and diazotizations and as auxiliary materials for chemical syntheses.

2. Description of the Related Art

The most common way, which can be easily carried out in the laboratory, of preparing alkyl nitrites is the reaction of sodium nitrite with strong acids, for example with sulphuric acid, in the presence of the appropriate alcohol:

$$2\ NaNO_2 + 2\ ROH + H_2SO_4 \rightarrow 2\ RONO + Na_2SO_4 + 2H_2O \qquad (1)$$

The process according to equation (1) is based on the high esterification rate of nitrous acid with the alcohol, it being possible to choose the reaction conditions such that the resulting alkyl nitrite can be removed from the reaction equilibrium as a gas, if appropriate by distilling off. The disadvantages of this process, however, lie in the use of expensive starting materials, such as, for example, sodium nitrite, and in the inevitable occurrence of large quantities of non-usable inorganic salts, in particular sodium sulphate. Furthermore, the alcohol used cannot in general be successfully brought to complete reaction, so that either corresponding losses have to be taken into account or a complicated treatment of the resulting waste water must be carried out.

Another process for preparing alkyl nitrites is based on the use of nitrogen oxides. In this case, preferably nitrogen monoxide, oxygen and the appropriate alcohol are caused to react with another, the following reactions taking place:

$$2\ NO + O_2 \rightarrow 2\ NO_3 \qquad (2)$$

$$NO + NO_2 \rightleftharpoons N_2O_3 \qquad (3)$$

$$ROH + N_2O_3 \rightarrow RONO + HNO_2 \qquad (4)$$

$$ROH + HNO_2 \rightarrow RONO + H_2O \qquad (5)$$

$$N_2O_3 + H_2O \rightarrow 2\ HNO_2 \qquad (6)$$

Here, it is attempted to allow the preparation of the sought-after alkyl nitrites to take place as far as possible only according to the reaction equations (2) to (5), water being obtained as the only waste substance. However, the reaction given in the reaction equation (6) is generally unavoidable, since the dinitrogen trioxide formed according to reaction equation (3) cannot only react with alcohol in the sense of equation (4) but can also react with the water produced according to equation (5). In the presence of adequate, in particular excess, quantities of the alcohol, however, the nitrous acid thus produced in the sense of equation (5) can be trapped to form the desired alkyl nitrite and water, and is thus not lost as a waste substance. A process taking place according to the described reactions is described, for example, in U.S. Pat. No. 2,831,882, where, for the preparation of isopropyl nitrite, nitrogen, nitrogen monoxide, nitrogen dioxide and isopropanol are introduced into a reaction vessel. German Patent Specification 11 56 775 describes the preparation of methyl nitrite by mixing nitrogen monoxide and oxygen in the ratio of 4,4:1 and introducing the gas mixture thus obtained into liquid methanol. U.S. Pat. No. 4,353,843 describes the reaction of a mixture of nitrogen monoxide and nitrogen dioxide, the proportion of the nitrogen monoxide being greater than that of the nitrogen dioxide, with gaseous methanol. EP 310 191, finally, describes the formation of lower alkyl nitrites by reaction of nitrogen monoxide, oxygen and the corresponding alcohols in a specific apparatus containing a reaction zone and a rectification zone, the water occurring in the course of the alkyl nitrite preparation being continuously removed by scrubbing out of the rising stream of product gas. The disadvantage of this process is the use of the nitrogen monoxide, which is technically poorly available in pure form. A further disadvantage is that, in order to suppress the formation, undesired in the process of EP 310 191, of nitric acid which results from the action of secondary reactions according to equations (7) to (9), excesses of nitrogen monoxide generally have to be used:

$$2\ NO_2 \rightleftharpoons N_2O_4 \qquad (7)$$

$$ROH + N_2O_4 \rightarrow RONO + HNO_3 \qquad (8)$$

$$N_2O_4 + H_2O \rightarrow HNO_2 + HNO_3 \qquad (9)$$

U.S. Pat. No. 2,739,166 describes a process according to which alkyl nitrites are obtained during the passing of gaseous nitrogen dioxide through the appropriate alcohols. Here, also according to the reaction equations (7) to (8), the desired alkyl nitrite is obtained mixed with nitric acid and unreacted excess alcohol. Basically, a procedure of this kind provides an advantage, since it permits the use of nitrogen dioxide, which is technically more available in pure form. The exothermicity of the reaction of nitrogen dioxide and alcohols to form alkyl nitrites and nitric acid is also less than that of nitrogen monoxide, oxygen and alcohols to form alkyl nitrites and water. With the elimination of the necessity of supplying oxygen and metering it as a function of the amount of nitrogen monoxide, fewer problems also result in the removal of the heat of reaction.

A disadvantage in the process described in U.S. Pat. No. 2,739,166, however, is that in the course of progressive reactions in the liquid phase, mixtures of alcohols and nitric acid result, the concentration of the latter increasing constantly. This is not only serious as regards safety aspects, the increased formation of secondary products, in particular the occurrence of toxic and highly explosive alkyl nitrates, must also be taken into account. It is also disadvantageous that the nitric acid residues occurring in the preparation of the alkyl nitrites contain at least still-unreacted alcohol, often also still-dissolved alkyl nitrite and also alkyl nitrate formed in secondary reactions and cannot be used further without complicated treatment. As regards the nitrogen dioxide used, this represents an economically unsatisfactory situation. There was therefore also the object, starting from technically readily available nitrogen dioxide, of developing a process for the preparation of alkyl nitrites which is suitable in particular for the synthesis of the technically interesting volatile compounds methyl nitrite and ethyl nitrite, does not lead to undesired secondary products, such as, for example, alkyl nitrates and provides the occurring nitric acid in a quality sufficient for further uses, in the most favourable case with the avoidance of additional cleaning measures. The far-reaching observance of the following requirements is essential for the successful operation of a process of this kind:

Nitrogen dioxide and the alcohol brought to reaction should as far as possible react completely with the formation of the desired alkyl nitrite and nitric acid.

Reaction control and reaction technology should be designed such that the undesired formation of secondary products such as alkyl nitrates is suppressed and the desired alkyl nitrite is obtained in as far as possible pure form.

The nitric acid resulting in the course of the reaction should, without an additional complicated operation such as, for example, an extraction, be separated from the desired alkyl nitrite completely and in a quality adequate for its further use.

The heat of reaction liberated in the course of the reactions occurring within the reactor should be led off.

As regards the safety requirements for the technical execution of the process to be sought, local overheatings and the occurrence of flammable mixtures must be avoided.

SUMMARY OF THE INVENTION

A process for preparing $C_1$–$C_6$-alkyl nitrites by reacting nitrogen dioxide with $C_1$–$C_6$-alcohols has been found, which is characterized in that, in a counterflow-operated column the alcohol or an alcohol/water mixture is fed into the upper part of the column and the nitrogen dioxide or a nitrogen dioxide/inert gas mixture is fed into the lower part of the column and the resulting alkyl nitrite is removed as the top product and the co-formed nitric acid is removed as the bottom product of the column.

DETAILED DESCRIPTION OF THE INVENTION

The process according to the invention possesses, for example, the following advantages:

As starting material it uses nitrogen dioxide such as occurs, for example, in industrial plant for the production of highly concentrated nitric acid and which is technically more available than nitrogen monoxide.

It permits the use of water-containing alcohols without this having a negative effect on the quality of the alkyl nitrites prepared; with the aid of the water content of the added alcohol, the degree of dilution of the nitric acid obtained at the bottom of the column can be selectively adjusted within wide limits.

It provides the nitric acid also occurring in the course of the reaction in high quality so that it can be used for further reactions without complicated purification.

It operates without an inevitable occurrence of inorganic salts and leads virtually exclusively to valuable materials, which is of great advantage from economic and ecological points of view. The range of by-products is extremely small in number and quantity.

It is suitable in particular for the preparation of the technically interesting low-boiling alkyl nitrites, such as in particular methyl nitrite and ethyl nitrite, preferably methyl nitrite.

In particular when water and/or inert gas are also used, it permits, by the consistent avoidance of flammable and explosive substance mixtures, substance concentrations and critical temperatures, all safety requirements to be complied with.

Compared with the prior art disclosed in U.S. Pat. No. 2,739,166, it was surprising in particular that the process according to the invention provides the reaction products, that is to say the respectively sought-after alkyl nitrite and the nitric acid also produced, in such a high purity that no further complicated cleaning operations are generally necessary. In particular it is surprisingly easy virtually completely to suppress the formation of secondary products, such as, for example, alkyl nitrates.

Alcohols for the process according to the invention are straight-chained and branched $C_1$–$C_6$-alkanols, preferably straight-chained $C_1$–$C_4$-alkanols and especially preferably methanol and ethanol. Methanol should be particularly mentioned.

The molar ratio of the metered-in alcohol to the fed-in nitrogen dioxide is 0.3 to 1:1, preferably 0.4 to 0.8:1 and especially preferably 0.5 to 0.7:1.

The molar ratio of the metered-in water to the fed-in nitrogen dioxide is 0 to 2:1, preferably 0.2 to 1.6:1 and especially preferably 0.8 to 1:1. The lower limit zero in the general range indicates that the process according to the invention can be carried out without metered-in water. The lower limit differing from zero in the preferred ranges indicates that the process according to the invention is carried out preferably in the presence of metered-in water.

The pressure below which the process according to the invention is carried out, is based, inter alia, on the substance data and phase equilibria of the components involved and also on considerations of economy in the sense of obtaining a maximum possible space-time yield and on the requirements of safety technology. Whereas, for example, in the case of the high-boiling alkyl nitrites, work must be carried out either under reduced pressure and/or at an elevated temperature level in order to be able to remove the required alkyl nitrite at the head of the reaction column, in the case of the low-boiling methyl nitrite, for example a pressure method is of advantage. In principle, the process according to the invention can accordingly be carried out both under standard pressure and also under reduced or elevated pressure. The pressure range from 0.5 to 10, preferably 0.8 to 8, especially preferably 1 to 5 bar comes into consideration.

For the temperature at which the process according to the invention is carried out, similar considerations apply. The temperature is chosen such that the substance data and phase equilibria of the components involved are taken into account, such that an economy in the sense of obtaining a maximum possible space-time yield is met and the requirements of the safety technology are satisfied. Whereas, for example, in the case of the higher boiling point alkyl nitrites, a higher thermal level must be used if required in order to be able to remove the desired alkyl nitrite at the top of the reaction column, in the case of the low-boiling methyl nitrite, for example, significantly lower temperatures are chosen. In the sense of these considerations, pressure and temperature are also suitably linked to one another. The temperature ranges 0° to 90° C., preferably 10° to 80° C., are suitable.

The nitrogen dioxide used according to the invention can be used as such or in the form of a mixture with inert gases. Such inert gases are, for example, nitrogen, carbon dioxide, argon, carbon monoxide, preferably nitrogen and carbon dioxide. Such an inert gas can be fed separately or as a mixture with nitrogen dioxide into the reactor. The volume ratio 1 (STP)/1 (STP) of the inert gas to the nitrogen dioxide is 0 to 5:1, preferably 0.1 to 3:1 and especially preferably 0.2 to 2:1.

The lower limit zero in the aforementioned volume ratio indicates that the process according to the invention can be carried out without the additional use of inert gases. The lower limit differing from zero in the preferred ranges indicates that the operation is carried out preferably in the presence of such an inert gas. The additional use of greater amounts of inert gas, for example, inert gas:nitrogen dioxide>2, in the process according to the invention, is of advantage in particular in the preparation of higher alkyl nitrites.

In order to carry out the process according to the invention, a reaction column is used which ensures a large phase boundary surface (gas/liquid) and ensures an intimate mixing of the liquid phase and the gas phase. This can be achieved by the installation of plates such as bubble-cap plates, sieve plates, valve plates, slotted plates etc., such as are conventional for a thermal separation, by packings of all kinds such as are conventional for thermal separation operations, or by equipping the column with irregular packings of all kinds or with regular packings of metal, ceramic, plastic, glass or other materials which are inert with respect to the reactants of the process according to the invention. Such columns with fittings, fillings or packings, and the fillings and packings themselves, are commercially available and known to the person skilled in the art. In the preferred manner, structured packings are used. The loading of the reaction apparatus, based on the entire amount of gas fed in (nitrogen dioxide and if required inert gas) is 10 to 3000, preferably 20 to 2000 and especially preferably 40 to 1000 l (STP)/l of free volume in the reaction column per hour. These ratios ensure an adequate residence time in order to achieve an as far as possible complete conversion.

If in carrying out the process according to the invention, water is metered in, this can be used separately or mixed with the alcohol. In a preferred manner the alcohol is introduced into the column above the metering in of the water. The product stream with the desired alkyl nitrite is removed from the reaction column as a gas at the top. The alcohol contained therein can be at least partially removed therefrom by cooling and/or by compressing the product stream; the alcohol thus reclaimed can be fed back into the reaction. Furthermore, the alkyl nitrite contained in the top stream which if appropriate is mixed with alcohol can also be at least partially removed therefrom by scrubbing with a suitable scrubbing medium, by intense cooling and/or by compressing the gaseous product stream; the inert gas remaining behind, if such was used, can be fed back into the reaction.

The alkyl nitrite prepared according to the invention can be used directly for further reactions, such as for nitrozations, diazotizations etc. If in these uses, the alkyl nitrite had not been separated from the inert gas also used, this inert gas is produced after the aforementioned reactions and can be fed therefrom back into the process according to the invention.

EXAMPLES

EXAMPLE 1

A carbon dioxide gas stream of 10 l/h was mixed with a nitrogen dioxide gas stream of 2.5 l/h (0.112 mol/h), temperature controlled at 25° C. and introduced into the lower end of a tube filled with Raschig rings and temperature controlled at 25° C. (dimensions: 1.6 cm diameter, 50 cm height).

In counterflow with this, 3 g/h of methanol and 3 g/h of water were fed in at the top end of the reactor.

From the gas stream obtained at the top of the column, samples were taken which were analyzed as regards their composition.

| Result: | carbon dioxide | 85% |
|---|---|---|
| | methyl nitrite | 11% |
| | methanol | 4% |

The liquid product produced at the bottom outlet of the column was collected and analyzed as regards its composition.

| Result: | water | 45% |
|---|---|---|
| | nitric acid | 55% |

It was not possible to detect methanol.

EXAMPLE 2

The experiment described in Example 1 was repeated, the gas stream and the reaction tube being temperature controlled at 40° C. instead of at 25° C. The gaseous top stream was analyzed.

| Result: | carbon dioxide | 84% |
|---|---|---|
| | methyl nitrite | 10% |
| | methanol | 6% |

The liquid product produced at the bottom outlet of the column was collected and analyzed as regards its composition.

| Result: | water | 45% |
|---|---|---|
| | nitric acid | 55% |

It was not possible to detect methanol.

EXAMPLE 3

A carbon dioxide gas stream of 10 l/h was mixed with a nitrogen dioxide gas stream of 7.5 l/h (0.335 mol/h), temperature controlled at 25° C. and introduced into a tube filled with Raschig rings and temperature controlled at 25° C. (dimensions: 1.6 cm diameter, 50 cm height).

In counterflow with this, 7 g/h of methanol and 7 g/h of water were fed in at the top end of the reactor.

From the gas stream produced at the top of the column, samples were taken which were analyzed as regards their composition.

| Result: | carbon dioxide | 67% |
|---|---|---|
| | methyl nitrite | 27% |

| | methanol | 6% |

The liquid product produced at the bottom outlet of the column was collected and analyzed as regards its composition.

| Result: | water | 39% |
| | nitric acid | 61% |

It was not possible to detect methanol.

EXAMPLE 4

A carbon dioxide gas stream of 20 l/h was mixed with a nitrogen dioxide gas stream of 12.3 l/h (0.549 mol/h), temperature controlled at 25° C. and introduced at the bottom end of a tube filled with Raschig rings and temperature controlled at 25° C. (dimensions: 1.6 cm diameter, 50 cm height).

In counterflow with this, 12 g/h of methanol and 12 g/h of water were fed in at the top end of the reactor.

From the gas stream produced at the top of the column, samples were taken which were analyzed as regards their composition.

| Result: | carbon dioxide | 71% |
| | methyl nitrite | 24% |
| | methanol | 5% |

The liquid product obtained at the bottom outlet of the column was collected and analyzed as regards its composition.

| Result: | water | 42% |
| | nitric acid | 58% |

It was not possible to detect methanol.

EXAMPLE 5

A carbon dioxide gas stream of 10 l/h was mixed with a nitrogen dioxide gas stream of 2.5 l/h (0.111 mol/h), temperature controlled at 25° C. and introduced at the bottom end of a tube filled with Raschig rings and temperature controlled at 25° C. (dimensions: 1.6 cm diameter, 50 cm height).

In counterflow with this, 22 g/h of methanol were fed in at the top end of the reactor.

From the gas stream obtained at the top of the column, samples were taken which were analyzed as regards their composition.

| Result: | carbon dioxide | 84% |
| | methyl nitrite | 11% |
| | methanol | 5% |

EXAMPLE 6

A carbon dioxide gas stream of 10 l/h was mixed with a nitrogen dioxide gas stream of 2.5 l/h (0.111 mol/h), temperature controlled at 30° C. and introduced at the bottom end of a tube filled with Raschig rings and temperature controlled at 30° C. (dimensions: 1.6 cm diameter, 50 cm height).

In counterflow with this, 4.2 g/h of ethanol and 3 g/h of water were fed in at the top end of the reactor.

From the gas stream produced at the top of the column, samples were taken which were analyzed as regards their composition.

| Result: | carbon dioxide | 82% |
| | ethyl nitrite | 13% |
| | ethanol | 5% |

The liquid product obtained at the bottom outlet of the column was collected and analyzed.

| Result: | water | 45% |
| | nitric acid | 55% |

It was not possible to detect ethanol.

EXAMPLE 7

The experiment described in Example 6 was repeated, the gas stream and the reaction tube being temperature controlled at 40° C. instead of at 30° C.

| Result: | carbon dioxide | 82% |
| | ethyl nitrite | 12% |
| | ethanol | 6% |

The liquid product produced at the bottom outlet of the column was collected and analyzed as regards its composition.

| Result: | water | 45% |
| | nitric acid | 55% |

It was not possible to detect ethanol.

COMPARATIVE EXAMPLE 1

A carbon dioxide gas stream of 10 l/h was mixed with a nitrogen dioxide gas stream of 2.5 l/h (0.111 mol/h) and introduced at 25° C. with stirring into 200 ml of methanol.

After only 3 hours it was possible to detect methyl nitrate in the resulting methanol/nitric acid mixture.

What is claimed is:

1. A process for the preparation of a $C_1$–$C_6$-alkyl nitrite by reacting nitrogen dioxide with a $C_1$–$C_6$-alcohol at a temperature of from 0° C. to 90° C. and a pressure of 0.5 to 10 bar in a counterflow-operated column wherein a mixture of said alcohol and water is fed into the upper part of the column and the nitrogen dioxide or a nitrogen dioxide/inert gas mixture is fed into the lower part of the column and the resulting alkyl nitrite is removed from the column as top product and the co-formed nitric acid is removed from the column as bottom product.

2. The process of claim 1, wherein a straight-chained $C_1$–$C_4$-alcohol is used.

3. The process of claim 2, wherein methanol or ethanol is used.

4. The process of claim 1, wherein the molar ratio of alcohol to nitrogen dioxide is 0.3 to 1:1.

5. The process of claim 4, wherein the molar ratio of alcohol to nitrogen dioxide is 0.4 to 0.8:1.

6. The process of claim 5, wherein the molar ratio of alcohol to nitrogen dioxide is 0.5 to 0.7:1.

7. The process of claim 1, wherein the molar ratio of water to nitrogen dioxide is 0 to 2:1.

8. The process of claim 7, wherein the molar ratio of water to nitrogen dioxide is 0.2 to 1.6:1.

9. The process of claim 8, wherein the molar ratio of water to nitrogen dioxide is 0.8 to 1:1.

10. The process of claim 1, wherein the operation is carried out under the pressure of 0.8 to 8 bar.

11. The process of claim 10, wherein the operation is carried out under the pressure of 1 to 5 bar.

12. The process of claim 1, wherein the operation is carried out at a temperature of 10° to 80° C.

13. The process of claim 1, wherein the volume ratio of inert gas to nitrogen dioxide, expressed in l (STP)/l (STP), is 0 to 5:1.

14. The process of claim 13, wherein the volume ratio of inert gas to nitrogen dioxide is 0.1 to 3:1.

15. The process of claim 14, wherein the volume ratio of inert gas to nitrogen dioxide is 0.2 to 2:1.

16. The process of claim 1, wherein the loading of the reaction column with the fed-in gases is 10 to 3000 l (STP)/l of free column volume per hour.

17. The process of claim 16, wherein the loading of the reaction column with the fed-in gases is 20 to 2000 l (STP)/l of free column volume per hour.

* * * * *